United States Patent
von Jako et al.

(10) Patent No.: US 8,821,511 B2
(45) Date of Patent: Sep. 2, 2014

(54) INSTRUMENT GUIDE FOR USE WITH A SURGICAL NAVIGATION SYSTEM

(75) Inventors: Ronald A. von Jako, Saugus, MA (US); Ella Zaslavsky, Marblehead, MA (US)

(73) Assignee: General Electric Company, Schenectady, NY (US)

( * ) Notice: Subject to any disclaimer, the term of this patent is extended or adjusted under 35 U.S.C. 154(b) by 1115 days.

(21) Appl. No.: 11/686,468

(22) Filed: Mar. 15, 2007

(65) Prior Publication Data

US 2008/0228195 A1 Sep. 18, 2008

(51) Int. Cl.
 A61B 19/00 (2006.01)
 A61B 17/00 (2006.01)
 A61B 17/34 (2006.01)

(52) U.S. Cl.
 CPC ... *A61B 19/5244* (2013.01); *A61B 2017/00725* (2013.01); *A61B 2019/5251* (2013.01); *A61B 2019/527* (2013.01); *A61B 2019/507* (2013.01); *A61B 2019/501* (2013.01); *A61B 2019/5268* (2013.01); *A61B 19/201* (2013.01); *A61B 19/5212* (2013.01); *A61B 17/3421* (2013.01); *A61B 2017/0046* (2013.01); *A61B 2019/5483* (2013.01); *A61B 17/3403* (2013.01); *A61B 2019/5291* (2013.01); *A61B 2017/00902* (2013.01); *A61B 19/54* (2013.01)
 USPC ............................................................ 606/130

(58) Field of Classification Search
 USPC ........ 606/130, 108, 96, 97, 98; 600/417, 429, 600/434
 See application file for complete search history.

(56) References Cited

U.S. PATENT DOCUMENTS

| | | | | |
|---|---|---|---|---|
| 5,676,673 | A * | 10/1997 | Ferre et al. | 606/130 |
| 5,888,034 | A * | 3/1999 | Greenberg | 408/115 R |
| 6,887,247 | B1 * | 5/2005 | Couture et al. | 606/96 |
| 7,153,308 | B2 * | 12/2006 | Peterson | 606/96 |
| 7,207,995 | B1 * | 4/2007 | Vandewalle | 606/104 |
| 7,226,456 | B2 * | 6/2007 | O'Neil et al. | 606/130 |
| 7,357,804 | B2 * | 4/2008 | Binder et al. | 606/96 |
| 7,488,327 | B2 * | 2/2009 | Rathbun et al. | 606/96 |
| 2001/0012942 | A1 * | 8/2001 | Estes et al. | 606/105 |
| 2003/0050558 | A1 * | 3/2003 | Bencini et al. | 600/425 |
| 2004/0073279 | A1 * | 4/2004 | Malackowski et al. | 607/88 |
| 2004/0077940 | A1 * | 4/2004 | Kienzle et al. | 600/424 |
| 2004/0171930 | A1 * | 9/2004 | Grimm et al. | 600/424 |
| 2004/0230200 | A1 * | 11/2004 | Peterson | 606/96 |
| 2005/0015092 | A1 * | 1/2005 | Rathbun et al. | 606/96 |
| 2005/0038444 | A1 * | 2/2005 | Binder et al. | 606/96 |
| 2006/0100637 | A1 * | 5/2006 | Rathbun et al. | 606/96 |
| 2007/0066878 | A1 * | 3/2007 | Worley et al. | 600/374 |

* cited by examiner

*Primary Examiner* — Thomas McEvoy
(74) *Attorney, Agent, or Firm* — Kenneth E. Horton; Kirton McConkie

(57) ABSTRACT

An instrument guide system for use with a surgical navigation system, the instrument guide system comprising a handle assembly, an instrument attachment assembly, a shaft connecting the handle assembly to the instrument attachment assembly, an electromagnetic sensor assembly removably mounted within an opening in the handle assembly, and an instrument removably attachable within a bore of the instrument attachment assembly.

12 Claims, 13 Drawing Sheets

INSTRUMENT GUIDE FOR USE WITH A SURGICAL NAVIGATION SYSTEM

BACKGROUND OF THE INVENTION

This disclosure relates generally to image-guided surgery (or surgical navigation), and more particularly, to an instrument guide for use in spinal surgical navigation procedures with surgical navigation systems.

Surgical navigation systems track the precise location of surgical instruments in relation to multidimensional images of a patient's anatomy. Additionally, surgical navigation systems use visualization instruments to provide the surgeon with co-registered views of these surgical instruments with the patient's anatomy.

During surgical procedures, it is beneficial to be able to track the position and trajectory of a surgical instrument, such as a drill bit, into a surgical site on a patient's body in order to ensure that the instrument is directed at the appropriate point in the body. In order to better track the position and trajectory of an instrument entering a surgical site, the instruments are often used with tracked instrument guides. The tracked instrument guides typically include a sensor assembly attached to the handle of the instrument guide. The sensor assembly may communicate with a computer to provide navigation and visualization information of the instrument on a display superimposed on an image of the patient's anatomy in the surgical field of interest.

Instrument guides are used in spinal surgery often for complex cases requiring precision placement of instrumentation, for example in the cervical spine. The approaches are anterior and/or posterior for various indications and procedures. Due to these different approaches, different instrument guides are utilized during certain instrument insertion steps (drill, k-wire, tap, and screw) of a procedure. Instrument guides allow proper positioning of the drill hole and tap to ensure different degrees of convergence patterns of screws at pre-selected angles. Instrument guides also help prevent toggling of different size drills and taps, minimizing the chance of losing cortical or bony tissue that helps later to ensure good bone screw purchase. The instrument guides also work as a safety stop to prevent over-tapping and bi-cortical breech by ending at pre-selected depths.

Therefore, it is desirable to provide navigation and visualization of an instrument guide for instrumentation used in spinal surgery.

BRIEF DESCRIPTION OF THE INVENTION

In one aspect, an instrument guide apparatus comprising a handle assembly, the handle assembly including a docking station formed therein for receiving an electromagnetic sensor assembly therein, an instrument attachment assembly, and a shaft connecting the handle assembly to the instrument attachment assembly.

In another aspect, an instrument guide system for use with a surgical navigation system, the instrument guide system comprising a handle assembly, an instrument attachment assembly, a shaft connecting the handle assembly to the instrument attachment assembly, an electromagnetic sensor assembly removably mounted within an opening in the handle assembly, and an instrument removably attachable within a bore of the instrument attachment assembly.

In yet another aspect, a calibration instrument for use with an instrument guide system, the calibration instrument comprising a cylindrically shaped rod having an outer diameter, a proximal end with a pointed tip, and a distal end with a pointed tip; and an engagement mechanism located toward the distal end thereof for mounting the calibration instrument into the instrument guide system.

In still yet another aspect, a guide instrument for use with an instrument guide system, the guide instrument comprising a cylindrically shaped tube having a bore extending therethrough, the cylindrical shaped tube having an outer diameter, a proximal end, and a distal end; and an engagement mechanism located near the distal end thereof for mounting the guide instrument into the instrument guide system.

Various other features, objects, and advantages of the invention will be made apparent to those skilled in the art from the accompanying drawings and detailed description thereof.

DETAILED DESCRIPTION OF THE INVENTION

In spinal surgical procedures, access to the body is obtained through one or more small percutaneous incision, mini-incision or one larger incision. Surgical instruments and guides are inserted through these openings and directed to a region of interest within the body. This would typically include the anterior lumbar spine, the junction for the lumbosacral space and the anterior cervical spine. Direction of the surgical instruments and guides through the body is facilitated by navigation technology wherein the real-time location of a surgical instrument or guide is measured and virtually superimposed on an image of the region of interest. The image may be a pre-acquired image, or an image obtained in near real-time or real-time using known imaging technologies such as computed tomography (CT), magnetic resonance (MR), positron emission tomography (PET), ultrasound, X-ray, or any other suitable imaging technology, as well as any combinations thereof.

Figure 1:
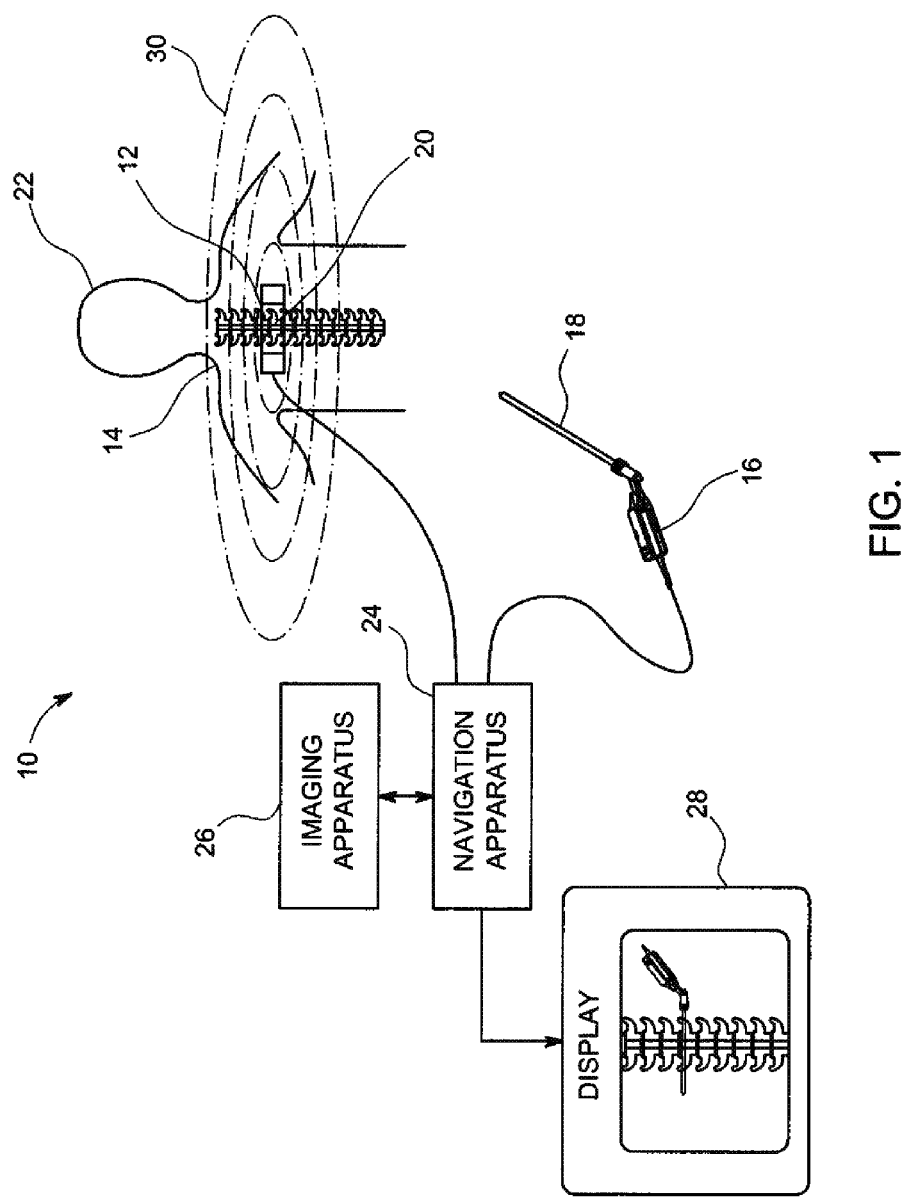
FIG. 1 is an exemplary schematic diagram of an embodiment of a surgical navigation system.

Referring now to the drawings, FIG. 1 illustrates an exemplary schematic diagram of an embodiment of a surgical navigation system 10. The surgical navigation system 10 includes at least one electromagnetic field generator 12 positioned proximate to a surgical field of interest 14, at least one electromagnetic sensor 16 attached to a trackable instrument guide 18 to which a surgical instrument may be inserted, the at least one electromagnetic sensor 16 communicating with and receiving data from the at least one electromagnetic field generator 12, a navigation apparatus 24 coupled to and receiving data from the at least one electromagnetic sensor 16 and the at least one electromagnetic field generator 12, an imaging apparatus 26 coupled to the navigation apparatus 24 for performing imaging on a patient 22 in the surgical field of interest 14, and a display 28 coupled to the navigation apparatus 24 for displaying imaging and tracking data from the imaging apparatus 26 and the navigation apparatus 24.

In an exemplary embodiment, the at least one electromagnetic field generator 12 may be attached to a dynamic reference apparatus 20 that may be attached to the patient 22 in the surgical field of interest 14. The at least one electromagnetic field generator 12 creates a local reference frame for the navigation apparatus 24 around the patient's anatomy.

The display 28 may be configured to show the real-time position and orientation of a model of the instrument guide 18 or surgical instrument inserted within the guide on a registered image of the patient's anatomy. The model of the instrument guide 18 or instrument may appear as a line rendering, a few simply shaded geometric primitives, or a realistic 3D model from a computer-aided design (CAD) file.

In an exemplary embodiment, the imaging apparatus 26 and the navigation apparatus 24 may be integrated into a single integrated imaging and surgical navigation system with integrated instrumentation and software.

The system 10 enables a surgeon to continually track the position and orientation of the instrument guide 18 or instrument during surgery. An electromagnetic field 30 is generated around the at least one electromagnetic field generator 12. The at least one electromagnetic sensor 16 detects the electromagnetic field 30 generated by the at least one electromagnetic field generator 12 attached to the dynamic reference apparatus 20. The at least one electromagnetic sensor 16 may be an electromagnetic field receiver. The electromagnetic field receiver may be a receiver array including at least one coil or at least one coil pair and electronics for digitizing magnetic field measurements detected by the receiver array. The at least one electromagnetic field generator 12 may be an electromagnetic field transmitter. The electromagnetic field transmitter may be a transmitter array including at least one coil or at least one coil pair. It should, however, be appreciated that according to alternate embodiments the dynamic reference apparatus 20 may include at least one electromagnetic field receiver attached thereto and the instrument guide 18 may include at least one electromagnetic field transmitter attached thereto.

The magnetic field measurements can be used to calculate the position and orientation of the instrument guide 18 or instrument according to any suitable method or system, After the magnetic field measurements are digitized using electronics, the digitized signals are transmitted from the at least one electromagnetic sensor 16 to the navigation apparatus 24. The digitized signals may be transmitted from the at least one electromagnetic sensor 16 to the navigation apparatus 24 using wired or wireless communication protocols and interfaces. The digitized signals received by the navigation apparatus 24 represent magnetic field information detected by the at least one electromagnetic sensor 16. The digitized signals are used to calculate position and orientation information of the instrument guide 18 or instrument. The position and orientation information is used to register the location of the instrument guide 18 or instrument to acquired imaging data from the imaging apparatus 26. The position and orientation data is visualized on the display 28, showing in real-time the location of the instrument guide 18 or instrument on pre-acquired or real-time images from the imaging apparatus 26. The acquired imaging data from the imaging apparatus 26 may include CT imaging data, MR imaging data, PET imaging data, ultrasound imaging data, X-ray imaging data, or any other suitable imaging data, as well as any combinations thereof. In addition to the acquired imaging data from various modalities, real-time imaging data from various real-time imaging modalities may also be available.

The navigation apparatus 24 is illustrated conceptually and may be implemented using any combination of dedicated hardware boards, digital signal processors, field programmable gate arrays, and processors. Alternatively, the navigation apparatus 24 may be implemented using an off-the-shelf computer with a single processor or multiple processors, with the functional operations distributed between processors. As an example, it may be desirable to have a dedicated processor for position and orientation calculations as well as a processor for visualization operations. The navigation apparatus 24 may be an electromagnetic navigation system utilizing electromagnetic navigation technology. However, other tracking or navigation technologies may be used.

Figure 2:
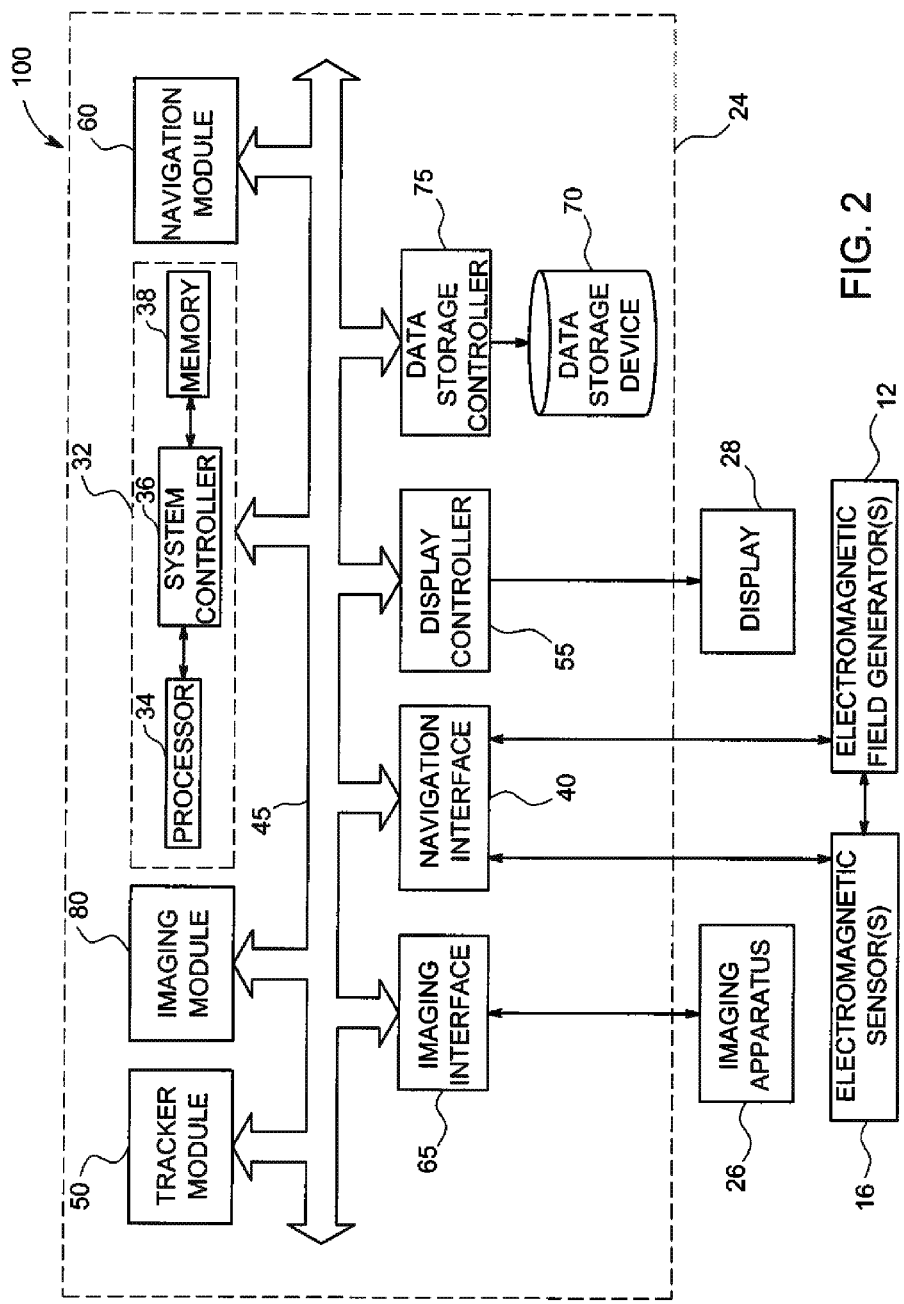
FIG. 2 is an exemplary block diagram of an embodiment of a surgical navigation system.

FIG. 2 illustrates an exemplary block diagram of an embodiment of a surgical navigation system 100. The surgical navigation system 100 is illustrated conceptually as a collection of modules, but may be implemented using any combination of dedicated hardware boards, digital signal processors, field programmable gate arrays, and processors. Alternatively, the modules may be implemented using an off-the-shelf computer with a single processor or multiple processors, with the functional operations distributed between the processors. As an example, it may be desirable to have a dedicated processor for position and orientation calculations as well as a dedicated processor for visualization operations. As a further option, the modules may be implemented using a hybrid configuration in which certain modular functions are performed using dedicated hardware, while the remaining modular functions are performed using an off-the-shelf computer. In the embodiment shown in FIG. 2, the navigation apparatus 24 includes a single computer 32 having a processor 34, a system controller 36 and memory 38. The operations of the modules and other components of the navigation apparatus 24 may be controlled by the system controller 36.

The surgical navigation system 100 includes at least one electromagnetic field generator 12 that is coupled to a navigation interface 40. The at least one electromagnetic field generator 12 generates at least one electromagnetic field that is detected by at least one electromagnetic field sensor 16. The navigation interface 40 receives digitized signals from at least one electromagnetic sensor 16. The navigation interface 40 includes at least one Ethernet port. The at least one Ethernet port may be provided, for example, with an Ethernet network interface card or adapter. However, according to various alternate embodiments, the digitized signals may be transmitted from the at least one electromagnetic sensor 16 to the navigation interface 40 using alternative wired or wireless communication protocols and interfaces.

The digitized signals received by the navigation interface 40 represent magnetic field information from the at least one electromagnetic field generator 12 detected by the at least one electromagnetic sensor 16. In the embodiment illustrated in FIG. 2, the navigation interface 40 transmits the digitized signals to a tracker module 50 over a local interface 45. The tracker module 50 calculates position and orientation information based on the received digitized signals. This position and orientation information provides a location of a surgical instrument or implant.

The tracker module 50 communicates the position and orientation information to a navigation module 60 over a local interface 45. As an example, this local interface 45 is a Peripheral Component Interconnect (PCI) bus. However, according to various alternate embodiments, equivalent bus technologies may be substituted.

Upon receiving the position and orientation information, the navigation module 60 is used to register the location of the surgical instrument or implant to acquired patient data. In the embodiment illustrated in FIG. 2, the acquired patient data is stored on a data storage device 70. The acquired patient data may include computed tomography data, magnetic resonance data, positron emission tomography data, ultrasound data, X-ray data, or any other suitable data, as well as any combinations thereof. By way of example only, the data storage device 70 is a hard disk drive, but other suitable storage devices may be used.

The acquired patient data is loaded into memory 38 from the data storage device 70. The acquired patient data is retrieved from the data storage device 70 by a data storage controller 75. The navigation module 60 reads from memory 38 the acquired patient data. The navigation module 60 registers the location of the instrument guide to acquired patient data, and generates image data suitable to visualize the patient image data and a representation of the instrument guide. The image data is transmitted to a display controller 55 over a local interface 45. The display controller 55 is used to output the image data to display 28.

In another exemplary embodiment, the surgical navigation system 100 may include an imaging apparatus 26 coupled to an imaging interface 65 for receiving real-time imaging data. The imaging data is processed in an imaging module 80. The imaging apparatus 26 provides the ability to display real-time position and orientation information of an instrument guide on the display 28.

While one display 28 is illustrated in the embodiment in FIG. 2, alternate embodiments may include various display configurations. Various display configurations may be used to improve operating room ergonomics, display different views, or display information to personnel at various locations.

Figure 3:
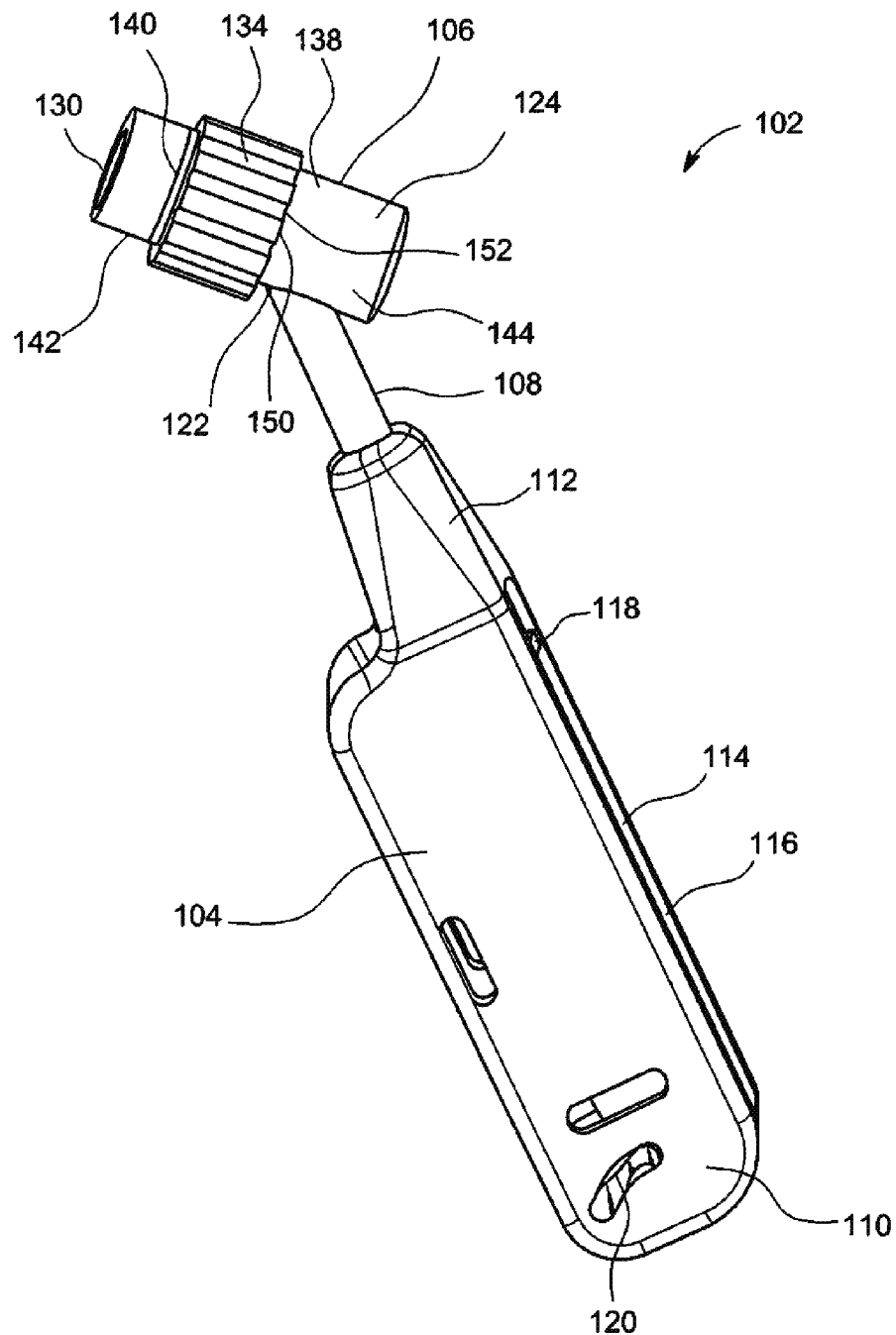
FIG. 3 is a side perspective view of an exemplary embodiment of an instrument guide apparatus.
Figure 4:
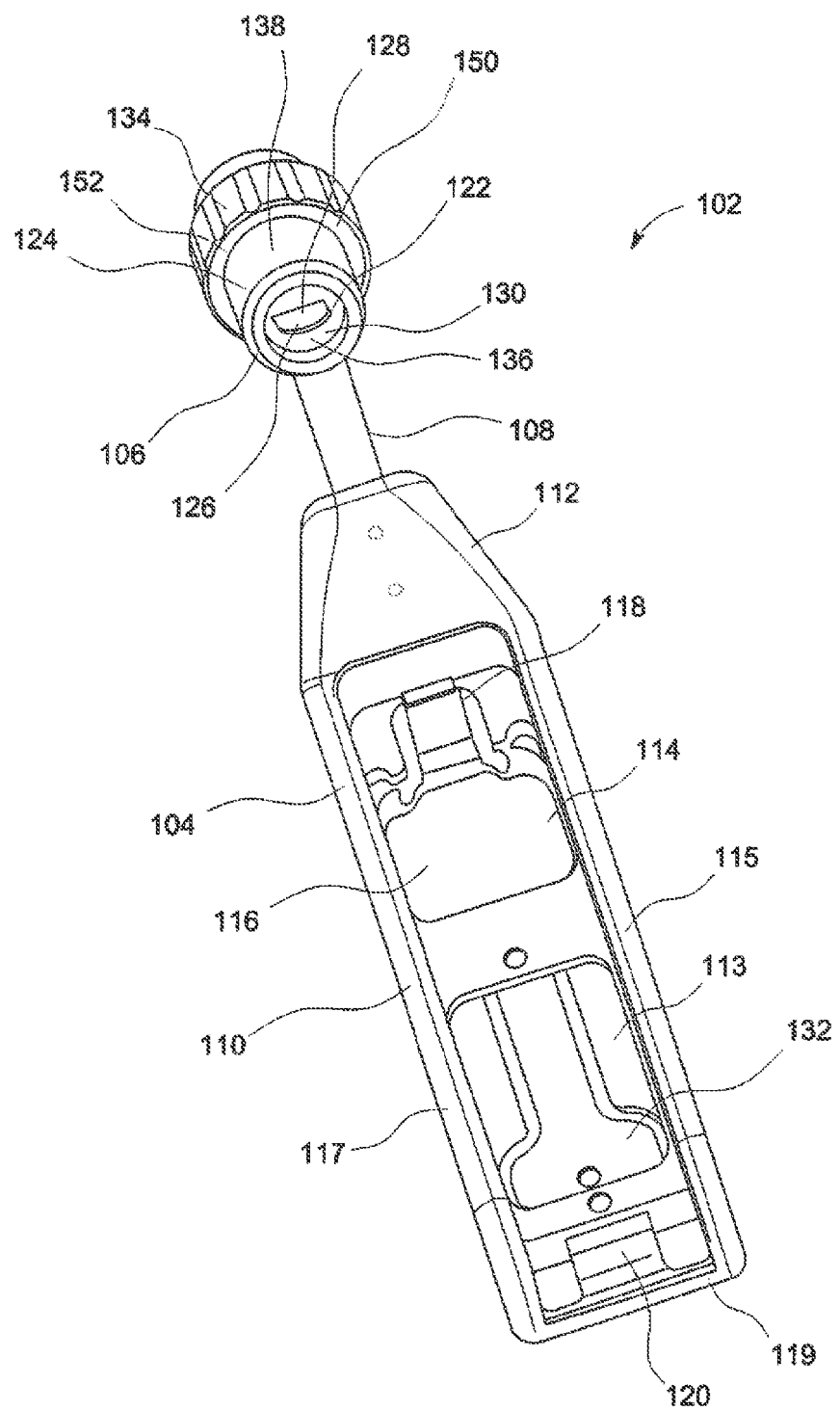
FIG. 4 is a top perspective view of the instrument guide apparatus of FIG. 3.
Figure 5:
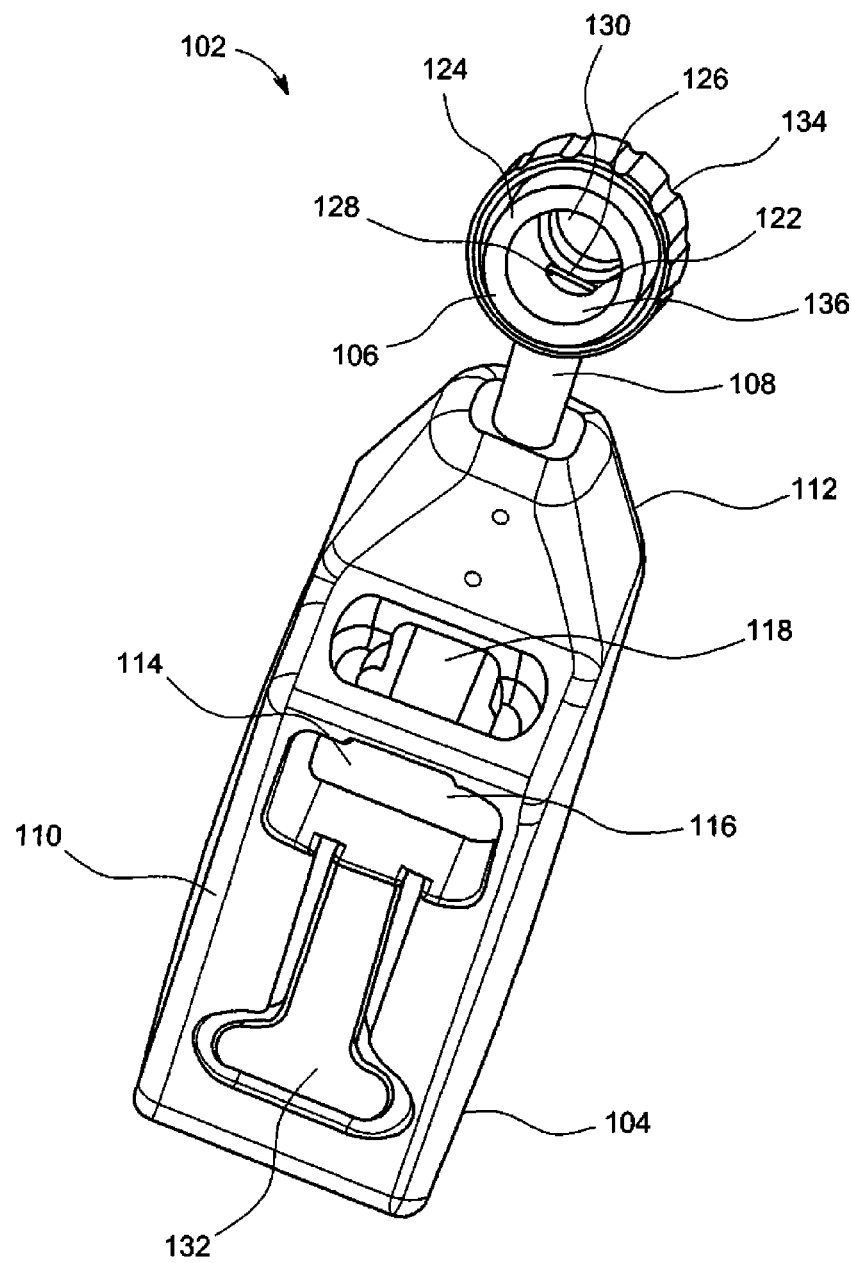
FIG. 5 is a bottom perspective view of the instrument guide apparatus of FIGS. 3 and 4.

FIGS. 3, 4 and 5 illustrate various views of an exemplary embodiment of an instrument guide apparatus 102. The instrument guide apparatus 102 comprises a handle assembly 104, an instrument attachment assembly 106, and a shaft 108 connecting the handle assembly 104 to the instrument attachment assembly 106.

The handle assembly 104 includes a handle body 110 and a handle stem 112. The handle body 110 includes an open top 113, two opposed sidewalls 115, 117 and a bottom wall 119. The open top 113, two opposed sidewalls 115, 117 and bottom wall 119 forms a docking station 114 for mounting an electromagnetic sensor assembly therein. The docking station 114 includes an opening 116 for receiving an electromagnetic sensor assembly therein, a locking member 118 at one end of the opening 116 for locking the electromagnetic sensor assembly in place, and an engagement member 120 at the opposite end thereof for keeping the electromagnetic sensor assembly engaged within the opening 116. The electromagnetic sensor assembly is secured between the locking member 118 and the engagement member 120 within the opening 116. The handle body 110 also includes a flexible switch member 132 in the bottom wall 119 thereof that functions as a push button switch. The flexible switch member 132 includes a fixed end 133 attached to a structural member 121 of the handle body 110 and a free end 135, opposite the fixed end 133, that may be pushed in by a user to activate a feature in the surgical navigation system software as further described below. Once the free end 135 of the flexible switch member 132 has been pushed in and released by a user, the free end 135 returns to its original position.

The handle stem 112 extends from the handle body 110 to the shaft 108. The shaft 108 extends from the end of the handle stem 112 through an opening 122 in a cylindrical member 124 of the instrument attachment assembly 106. The end 126 of the shaft 108 extends up through the opening 122 and includes a tab 128 to secure and prevent a calibration or guide instrument inserted within a central bore 130 of the cylindrical member 124 from rotating.

The instrument attachment assembly 106 includes the cylindrical member 124 having a central bore 130 extending therethrough and a fastening member 134 extending around an outer surface 138 of the cylindrical member 124. The cylindrical member 124 receives a calibration or guide instrument within its central bore 130, the instrument extending through the central bore 130.

The cylindrical member 124 has an inner surface 136 and an outer surface 138. The inner surface 136 forming the central bore 130, and the outer surface 138 having a lip 140 extending around an outer circumference of an upper portion 142 thereof to prevent the fastening member 134 from sliding off the upper portion 142 of the cylindrical member 124. The shaft 108 extending into the opening 122 on a lower portion 144 of the cylindrical member 124 prevents the fastening member 134 from sliding off the lower portion 144 thereof. The fastening member 134 is thus, movable along the outer surface 138 of the cylindrical member 124 between the shaft 108 and the lip 140.

The fastening member 134 has a flange 150 extending around the circumference of one of its open ends 152 and extending inwardly to engage the lip 140 extending around the outer surface 138 of the upper portion 142 of cylindrical member 124. The fastening member 134 includes threads on its inner surface for securing a calibration or guide instrument within the central bore 130 of the cylindrical member 124. The fastening member 134 is used for locking and releasing a calibration or guide instrument to and from the cylindrical member 124.

Figure 6:
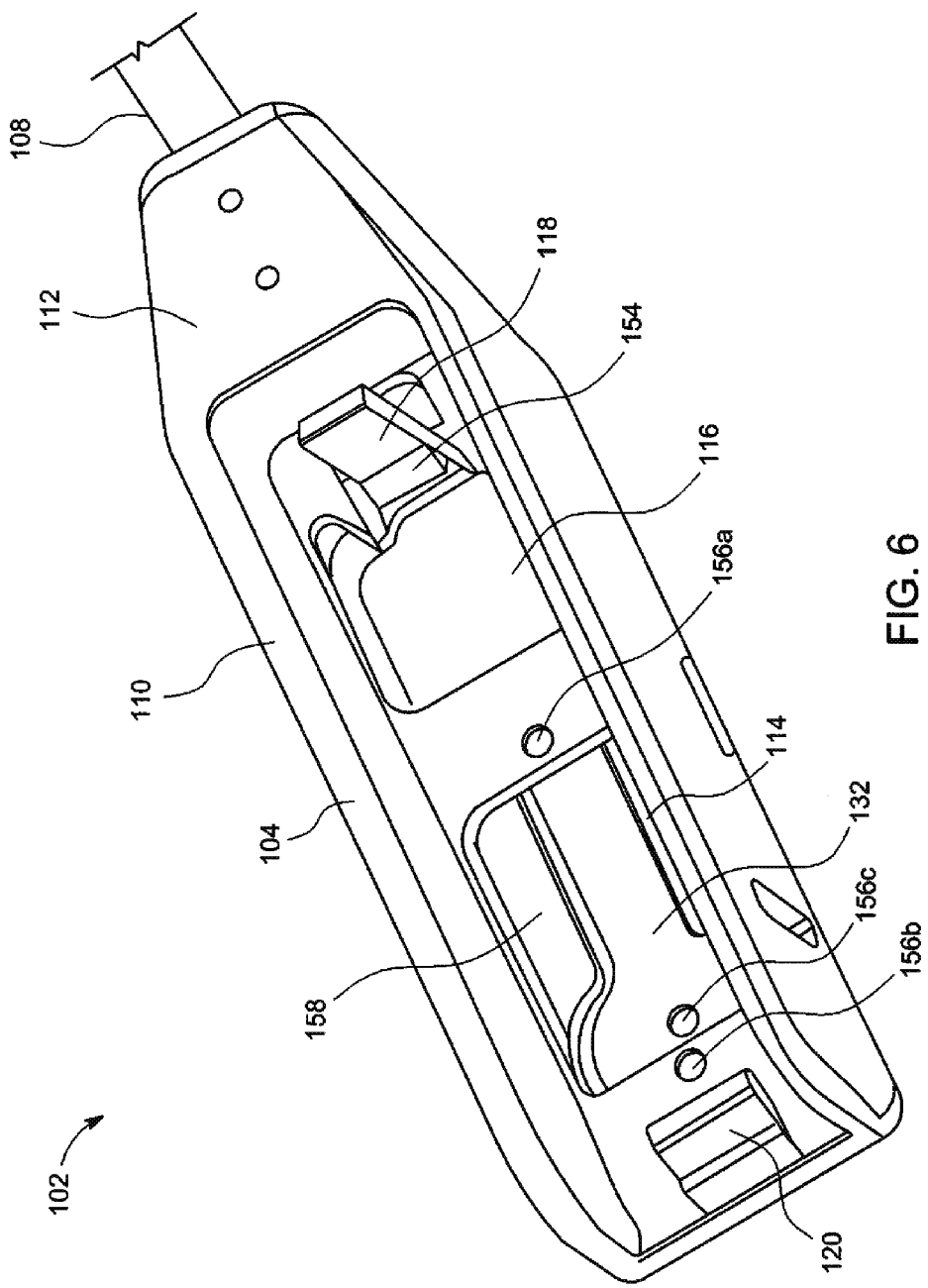
FIG. 6 is an enlarged top perspective view of an exemplary embodiment of a handle assembly of an instrument guide apparatus.

FIG. 6 illustrates an enlarged view of an exemplary embodiment of the handle assembly 104 of the instrument guide apparatus 102. As stated above, the handle assembly 104 includes a handle body 110 and a handle stem 112. The handle body 110 includes an open top 113, two opposed sidewalls 115, 117 and a bottom wall 119. The open top 113, two opposed sidewalls 115, 117 and bottom wall 119 forms a docking station 114 for mounting an electromagnetic sensor assembly therein. The electromagnetic sensor assembly enabling tracking and navigation of the instrument guide. The docking station 114 includes an opening 116 for receiving an electromagnetic sensor assembly therein, a locking member 118 at one end of the opening 116 for locking the electromagnetic sensor assembly in place, and an engagement member 120 at the opposite end thereof for keeping the electromagnetic sensor assembly engaged within the opening 116. The electromagnetic sensor assembly is secured between the locking member 118 and the engagement member 120 within the opening 116. The handle body 110 also includes a flexible switch member 132 in the bottom wall 119 thereof that functions as a push button switch. The flexible switch member 132 includes an inner surface 137 and an outer surface 139. The flexible switch member 132 also includes a fixed end 133 attached to a structural member 121 of the handle body 110 and a free end 135, opposite the fixed end 133, that may be pushed in by a user to activate a feature in the surgical navigation system software as further described below. Once the free end 135 of the flexible switch member 132 has been pushed in and released by a user, the free end 135 returns to its original position.

The locking member 118 is flexible and includes a tab 154 to lock and release the electromagnetic sensor assembly in place within the opening 116 of the docking station 114. The locking member 118 and tab 154 are bent back towards the handle stem 112 when installing an electromagnetic sensor assembly with the tab 154 engaging a portion of the electromagnetic sensor assembly to lock it in place. To remove the electromagnetic sensor assembly, the locking member 118 and tab 154 are bent back again towards the handle stem 112 to release the tab 154 from the portion of the electromagnetic sensor assembly so that it may be pulled out. The engagement member 120 is a spring-like member or is made from a flexible spring-like material that deforms when an electromagnetic sensor assembly is installed, and pushes against the electromagnetic sensor assembly, pushing it towards the locking member 118 and tab 154 to hold the electromagnetic sensor assembly in place. The engagement member 120 deforms when pressure or force is applied against it and returns to its original shape when no pressure or force is applied against it.

The handle body 110 also includes a plurality of cavities 156, 157 formed in structural members 121, 123 in the bottom of opening 116 of docking station 114. These cavities 156, 157 are designed to be populated with magnets (not shown) and located adjacent to Hall effect sensor circuitry on an electromagnetic sensor assembly when it is installed in opening 116 of docking station 114. The Hall effect sensor circuitry detects the presence of magnets. A magnet may or may not be installed in each cavity. The presence or lack of a magnet in each cavity provides a bit pattern (magnet, no magnet) that is detected by the Hall effect sensor circuitry and interpreted by software in the surgical navigation system to determine the specific instrument or guide instrument being used. Each surgical instrument or guide instrument is associated with a particular bit pattern in the software, so that the software can identify the particular instrument or guide instrument being used. The presence (1) or no presence (0) of a magnet provides the bit pattern (magnet (1), no magnet (0)) to activate the Hall effect sensor circuitry, enabling the surgical navigation system to recognize and identify the type of instrument or guide instrument being used.

The flexible switch member 132 includes a cavity 158 formed in the inner surface 137 of free end 135 at the bottom of opening 116 of docking station 114. The cavity 58 is designed to be populated with a magnet (not shown) and located a distance from Hall effect sensor circuitry on an electromagnetic sensor assembly when it is installed in opening 116 of docking station 114. In this position, the magnet in cavity 158 is too far away from the Hall effect sensor circuitry on the electromagnetic sensor assembly so that it does not sense the magnet. The magnet in cavity 158 is farther away from the Hall effect sensor circuitry on the electromagnetic sensor assembly than the magnets in cavities 156 and 157 would be. When a user pushes in free end 135 of flexible switch member 132 towards the Hall effect sensor circuitry on the electromagnetic sensor assembly, the magnet in cavity 158 moves closer to the Hall effect sensor circuitry, which detects the magnet and activates a feature in the navigation system software. This feature could be to freeze the virtual representation and virtual trajectory line of the instrument guide shown on the display, or any other feature. For example, a second push of free end 135 of flexible switch member 132 could be to clear the virtual trajectory line of the instrument guide shown on the display.

Figure 7:
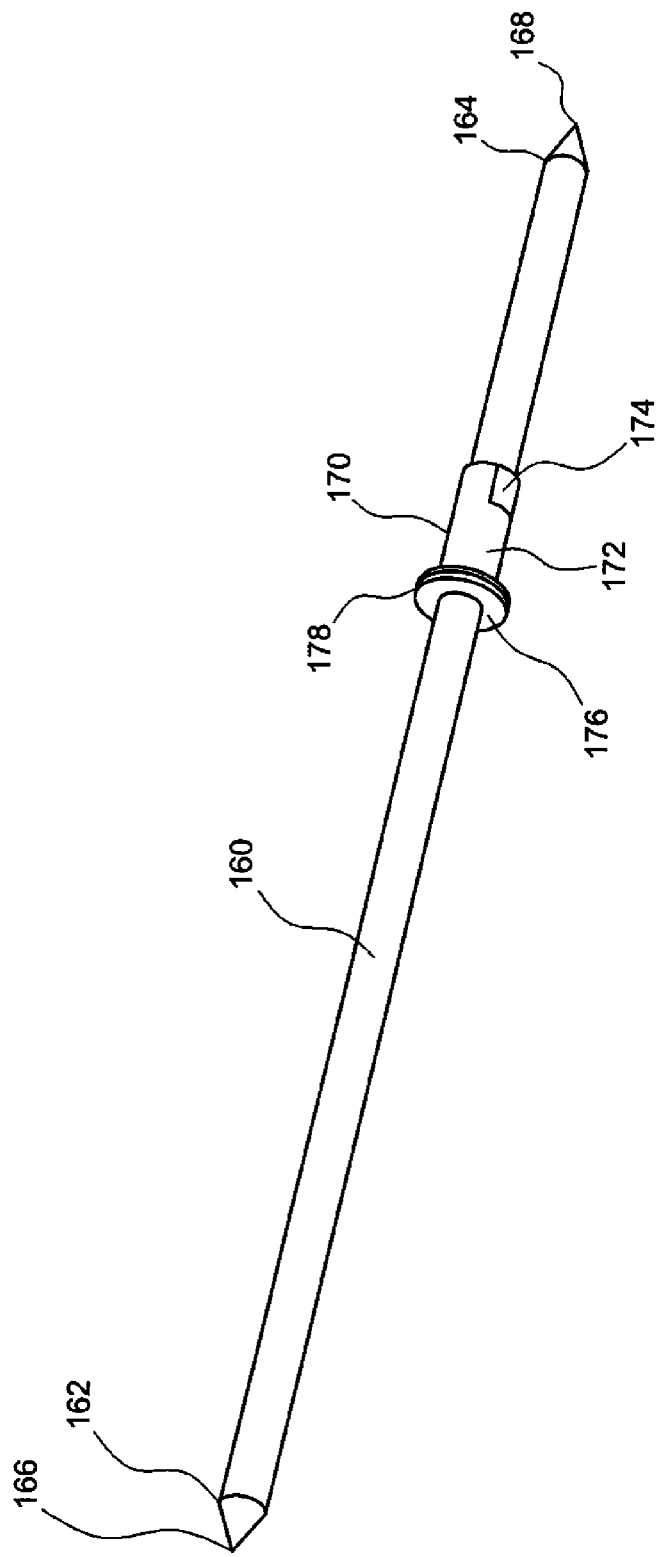
FIG. 7 is a perspective view of an exemplary embodiment of a calibration instrument attachable to an instrument guide apparatus.

FIG. 7 illustrates an exemplary embodiment of a calibration instrument 160 attachable to the instrument guide apparatus 102. The calibration instrument 160 is a cylindrically shaped rod with two pointed ends. The calibration instrument 160 includes a proximal end 162 that tapers to a point 166 and a distal end 164 that tapers to a point 168. The calibration instrument 160 includes a front pointed tip 166 and a rear pointed tip 168 used in a calibration procedure. The calibration instrument 160 further includes, an engagement mechanism 170 located toward the distal end 164 thereof. The engagement mechanism 170 includes an engagement cylinder 172 having an outer diameter greater than the outer diameter of the cylindrically shaped rod. The engagement cylinder 172 includes at least one flat groove 174, or other keying feature, at one end thereof and a radially extending disk 176 at the opposite end thereof. The at least one flat groove 174 is designed to mate with the tab 128 of the end 126 of shaft 108 to secure and prevent the calibration instrument from rotating. The disk 176 having an outer circumference surface 178 that is threaded for engaging the threads on the inner surface of fastening member 134 on the instrument attachment assembly 106.

In operation, the distal end 164 of the calibration instrument 160 is inserted into the central bore 130 of the cylindrical member 124 of the instrument attachment assembly 106 until the tab 128 engages the flat groove 174. The fastening member 134 is then brought up around the disk 176 and tightened to secure the calibration instrument 160 in place within the instrument attachment assembly 106.

To ensure the virtual instrument image accuracy, an instrument guide system is calibrated with calibration instruments 160, one for each guide instrument length. Therefore, there is a set of calibration instruments 160, each having a different length to correspond to the different lengths of the guide instruments to be used in a surgical procedure. Each calibration instrument 160 can be easily locked and released to and from the instrument attachment assembly 106 using the same fastening features described above.

Figure 8:
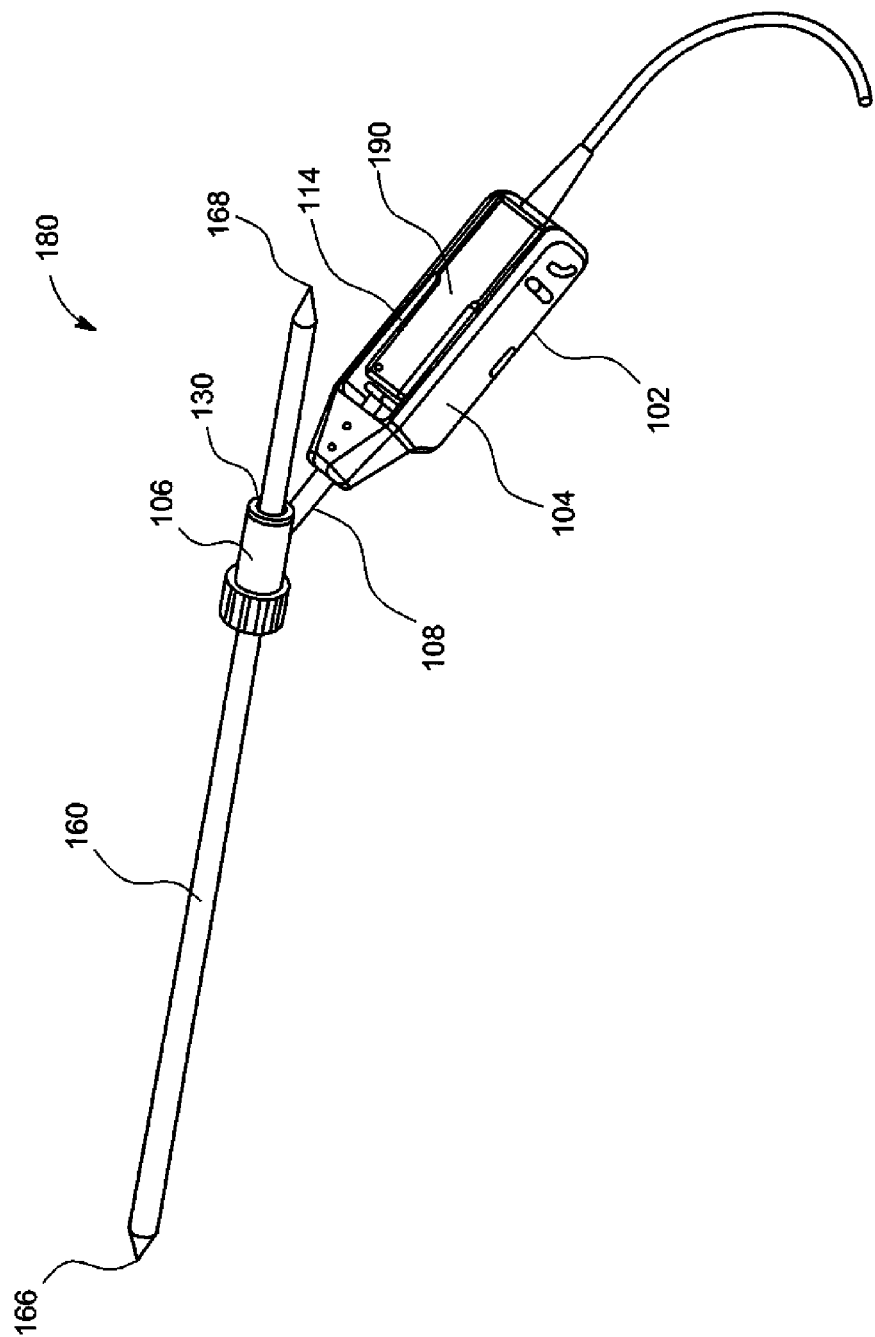
FIG. 8 is a perspective view of an exemplary embodiment of a trackable instrument guide system with a calibration instrument and an electromagnetic sensor assembly attached to an instrument guide apparatus.

FIG. 8 illustrates an exemplary embodiment of a trackable instrument guide system 180 with a calibration instrument 160 and an electromagnetic sensor assembly 190 attached to the instrument guide apparatus 102. The instrument guide system 180 comprises a handle assembly 104, an instrument attachment assembly 106, a shaft 108 connecting the handle assembly 104 to the instrument attachment assembly 106, an electromagnetic sensor assembly 190 removably mounted within a docking station 114 of the handle assembly 104, and a calibration instrument 160 removably attachable within the central bore 130 of the instrument attachment assembly 106. The calibration instrument 160 may be from a set of calibration instruments having different lengths that correspond to the different lengths of guide instruments. The instrument guide system 180 is intended for multiple uses in surgical procedures to guide instrumentation with surgical navigation.

The electromagnetic sensor assembly 190 is configured to receive electromagnetic signals as part of the surgical navigation system. For example, an electromagnetic field generator is located in a fixed position relative to a surgical field of interest. The electromagnetic field generator generates an electromagnetic field to be received by an electromagnetic sensor of the electromagnetic sensor assembly 190. The electromagnetic sensor and the electromagnetic field generator are coupled to a computer such that the computer may calculate and determine the position, orientation and trajectory of the electromagnetic sensor relative to the electromagnetic field generator. The computer provides visualization and navigation of the instrument guide system 180 for instrumentation used in various surgical procedures.

In order to prepare the instrument guide system 180 for use during a surgical procedure and to ensure virtual instrument image accuracy, the instrument guide system 180 is first calibrated with calibration instruments 160, one for each guide instrument length being used. The calibration instrument 160 is installed within the central bore 130 of the instrument attachment assembly 106. The positions of the tips 166, 168 of the calibration instrument 160 are located relative to the electromagnetic sensor assembly 190 by touching the front tip 166 to a reference point of known location and touching the rear tip 168 to a reference point of known location. The reference point of known location may be the dynamic reference apparatus 20. The position and trajectory of the calibration instrument 160 relative to the electromagnetic sensor assembly 190 is then stored in the computer of the surgical navigation system.

Figure 9:
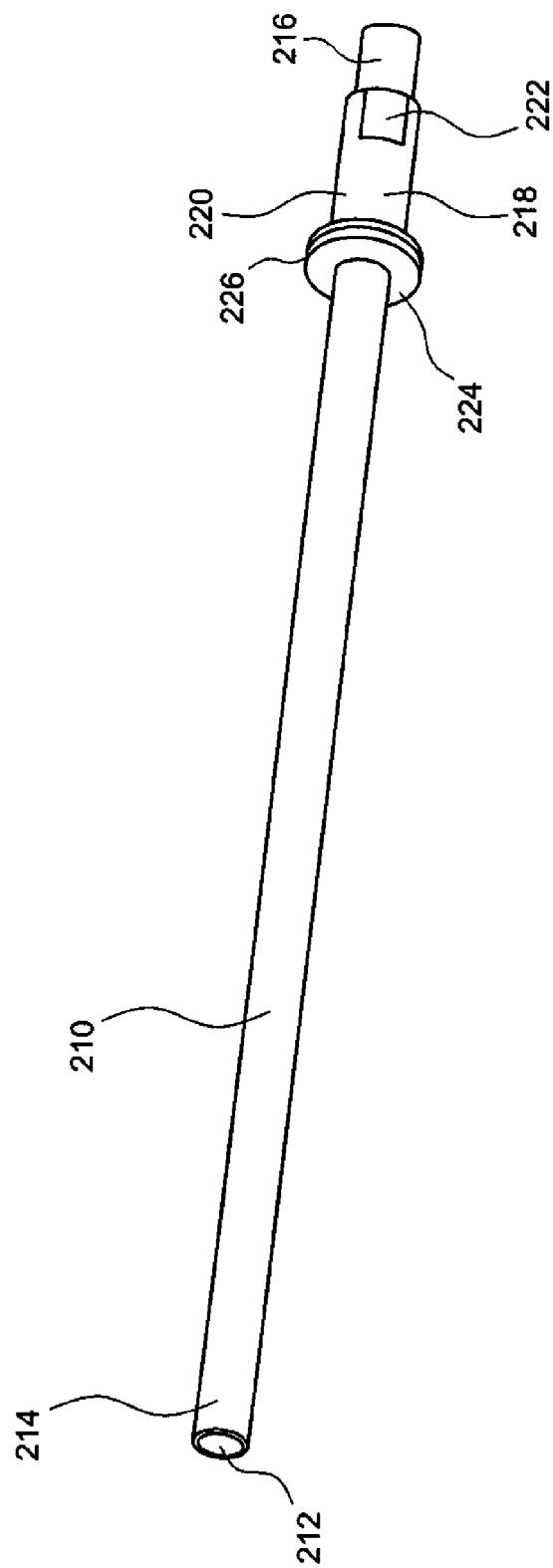
FIG. 9 is a perspective view of an exemplary embodiment of a guide instrument attachable to an instrument guide apparatus.

FIG. 9 illustrates an exemplary embodiment of a guide instrument 210 attachable to the instrument guide apparatus 102. The guide instrument 210 is generally cylindrical in shape and includes a bore 212 extending therethrough. The bore 212 has an inner diameter of a size appropriate to accommodate a drill bit, guide pin, guidewire, k-wire, awl, tap, probe, screw or other insertable instrument. The guide instrument 210 includes a proximal end 214 and a distal end 216. The guide instrument 210 further includes an engagement mechanism 218 located near the distal end 216 thereof. The engagement mechanism 218 includes an engagement cylinder 220 having an outer diameter greater than the outer diameter of the guide instrument 210. The engagement cylinder 220 includes at least one flat groove 222, or other keying feature, at one end thereof and a radially extending disk 224 at the opposite end thereof. The at least one flat groove 222 is designed to mate with the tab 128 of the end 126 of shaft 108 to secure and prevent the guide instrument from rotating. The disk 224 having an outer circumference surface 226 that is threaded for engaging the thread on the inner surface of fastening member 134 on the instrument attachment assembly 106.

The guide instrument 210 may be designed for multiple uses and made of a material typically used for multiple use surgical instruments, or designed for a single use and made of a disposable radiolucent material.

In operation, the distal end 216 of the guide instrument 210 is inserted into the central bore 130 of the cylindrical member 124 of the instrument attachment assembly 106 until the tab 128 engages the flat groove 222. The fastening member 134 is then brought up around the disk 224 and tightened to secure the guide instrument 210 in place within the instrument attachment assembly 106.

The guide instruments 210 may vary in size (outer and inner diameters) and length (some have adjustable lengths for adjusting depth), and also by shape (some are single barreled and some are double barreled). Therefore, there is a set of guide instruments 210, each having different inner diameters, outer diameters, and lengths to correspond to the different surgical instruments to be used in a surgical procedure. Each guide instrument 210 can be easily locked and released to and from the instrument attachment assembly 106 using the same fastening features described above.

Figure 10:
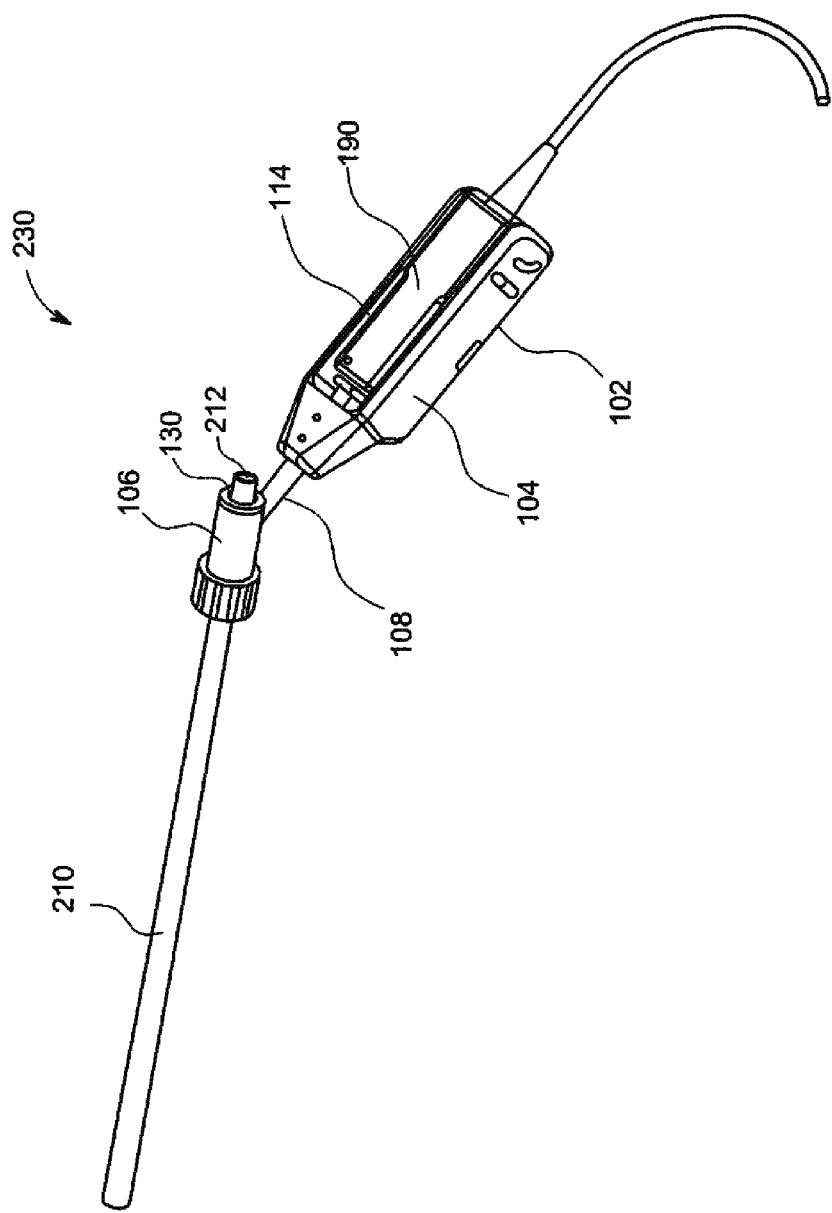
FIG. 10 is a perspective view of an exemplary embodiment of a trackable instrument guide system with a guide instrument and an electromagnetic sensor assembly attached to an instrument guide apparatus.

FIG. 10 illustrates an exemplary embodiment of a trackable instrument guide system 230 with a guide instrument 210 and an electromagnetic sensor assembly 190 attached to the instrument guide apparatus 102. The instrument guide system 230 comprises a handle assembly 104, an instrument attachment assembly 106, a shaft 108 connecting the handle assembly 104 to the instrument attachment assembly 106, an electromagnetic sensor assembly 190 removably mounted within a docking station 114 of the handle assembly 104, and a guide instrument 210 removably attachable within the central bore 130 of the instrument attachment assembly 106. The guide instrument 210 may be from a set of guide instruments having different inner diameters, outer diameters, and lengths. The instrument guide system 230 is configured to receive a surgical instrument within the bore 212 of the guide instrument 210. The instrument guide system 230 is intended for multiple uses in surgical procedures to guide instrumentation with surgical navigation.

The electromagnetic sensor assembly 190 is configured to receive electromagnetic signals as part of the surgical navigation system. For example, an electromagnetic field generator is located in a fixed position relative to a surgical field of interest. The electromagnetic field generator generates an electromagnetic field to be received by an electromagnetic sensor on the electromagnetic sensor assembly 190. The electromagnetic sensor and the electromagnetic field generator are coupled to a computer such that the computer may calculate and determine the position, orientation and trajectory of the electromagnetic sensor relative to the electromagnetic field generator. The computer provides visualization and navigation of the instrument guide system 230 for instrumentation used in various surgical procedures.

Once the guide instrument is properly calibrated and trackable, the surgeon inserts a desired instrument into the guide instrument. The position of the instrument is fixed and known relative to the electromagnetic sensor. The electromagnetic sensor communicates with the computer in the surgical navigation system such that the computer can calculate, determine, and show on a display, the position and trajectory of the guide instrument relative to the patient's anatomy. Thus, the surgeon can track the movement of the guide instrument relative to the image on the display during surgery. Because the position of the instrument is fixed and known relative to the electromagnetic sensor, the computer can calculate, determine and display the position of the proximal end of the instrument relative to the patient's anatomy.

Figure 11A:
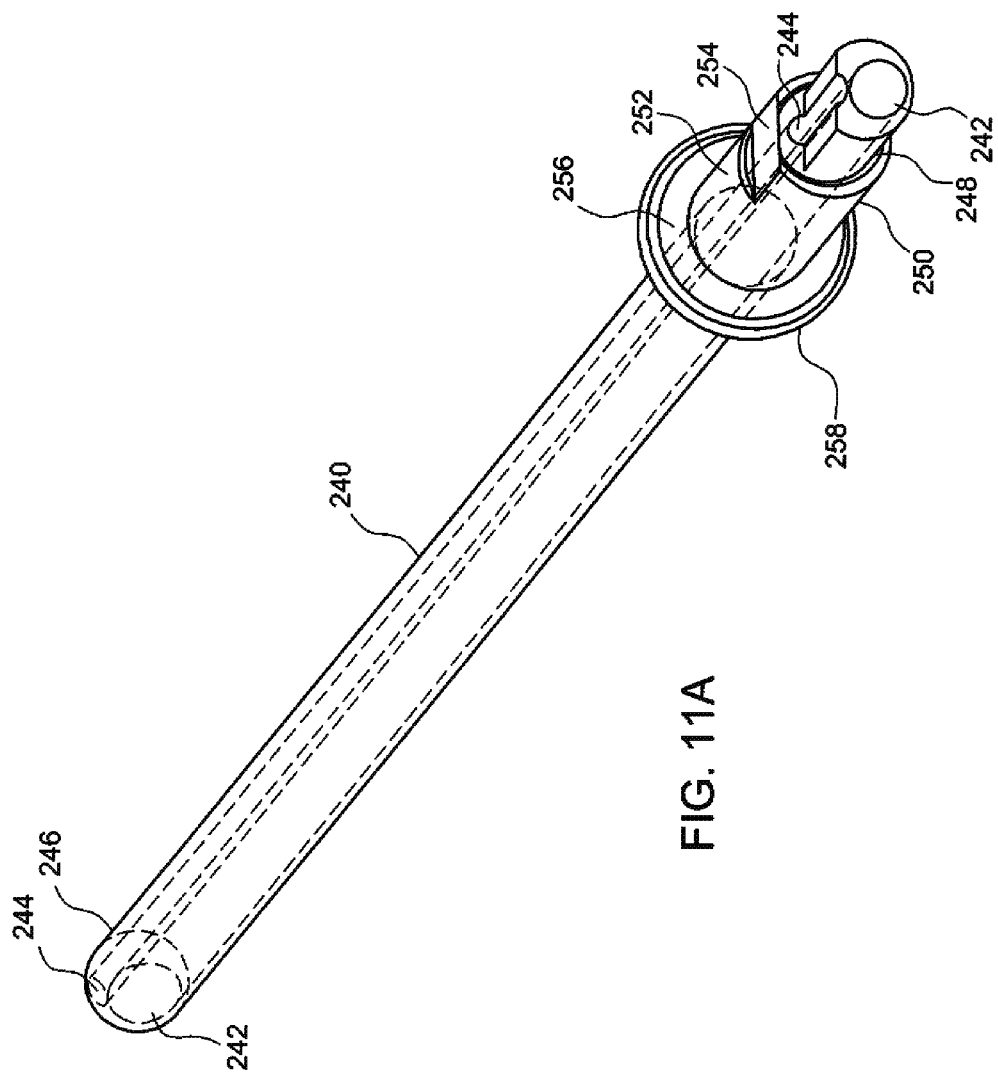
FIG. 11A is a perspective rear view of an exemplary embodiment of a guide instrument attachable to an instrument guide apparatus.
Figure 11B:
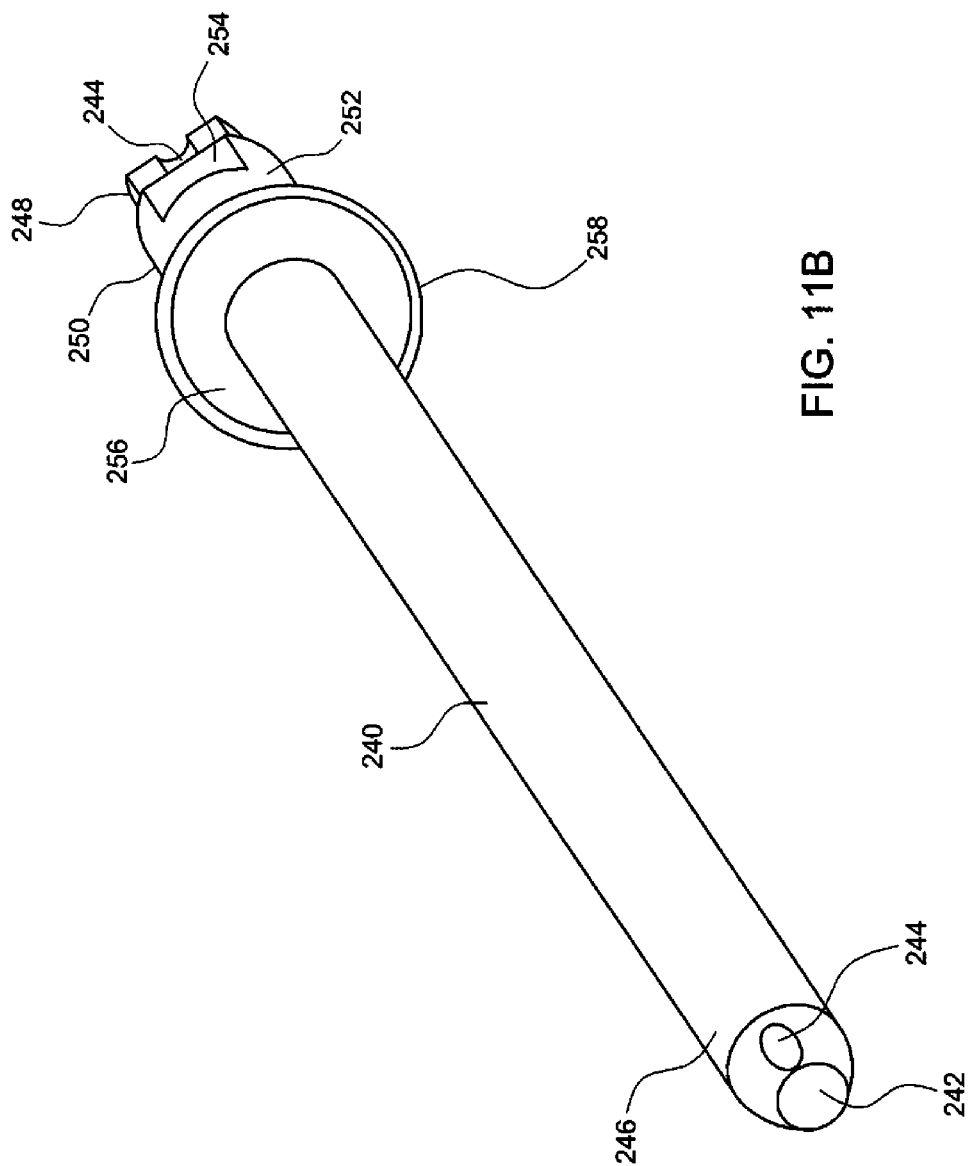
FIG. 11B is a perspective front view of the guide instrument of FIG. 11A.

FIGS. 11A and 11B illustrate an exemplary embodiment of a guide instrument 240 attachable to the instrument guide apparatus 102. The guide instrument 240 is generally cylindrical in shape and includes a first bore 242 extending therethrough and a second bore 244 extending therethrough, the second bore 244 being adjacent to first bore 242. The first bore 242 has an inner diameter of a size appropriate to accommodate a drill bit, guide pin, guidewire, k-wire, awl, tap, probe, screw or other insertable instrument. The second bore 244 has an inner diameter of a size appropriate to accommodate a catheter, endoscope, fiberscope, video endoscope or other insertable instrument. For example, the second bore 244 could be used to accept a catheter with irrigation and aspiration capabilities, a high intensity fiber optic light cable, or a rigid or flexible scope. The guide instrument 240 includes a proximal end 246 and a distal end 248. The guide instrument 240 further includes an engagement mechanism 250 located near the distal end 248 thereof. The engagement mechanism 250 includes an engagement cylinder 252 having an outer diameter greater than the outer diameter of the guide instrument 240. The engagement cylinder 252 includes at least one flat groove 254, or other keying feature, at one end thereof and a radially extending disk 256 at the opposite end thereof. The at least one flat groove 254 is designed to mate with the tab 128 of the end 126 of shaft 108 to secure and prevent the guide instrument from rotating. The disk 256 having an outer circumference surface 258 that is threaded for engaging the thread on the inner surface of fastening member 134 on the instrument attachment assembly 106.

The guide instrument 240 may be designed for multiple uses and made of a material typically used for multiple use surgical instruments, or designed for a single use and made of a disposable radiolucent material.

In operation, the distal end 248 of the guide instrument 240 is inserted into the central bore 130 of the cylindrical member 124 of the instrument attachment assembly 106 until the tab 128 engages the flat groove 254. The fastening member 134 is then brought up around the disk 256 and tightened to secure the guide instrument 240 in place within the instrument attachment assembly 106.

Figure 12:
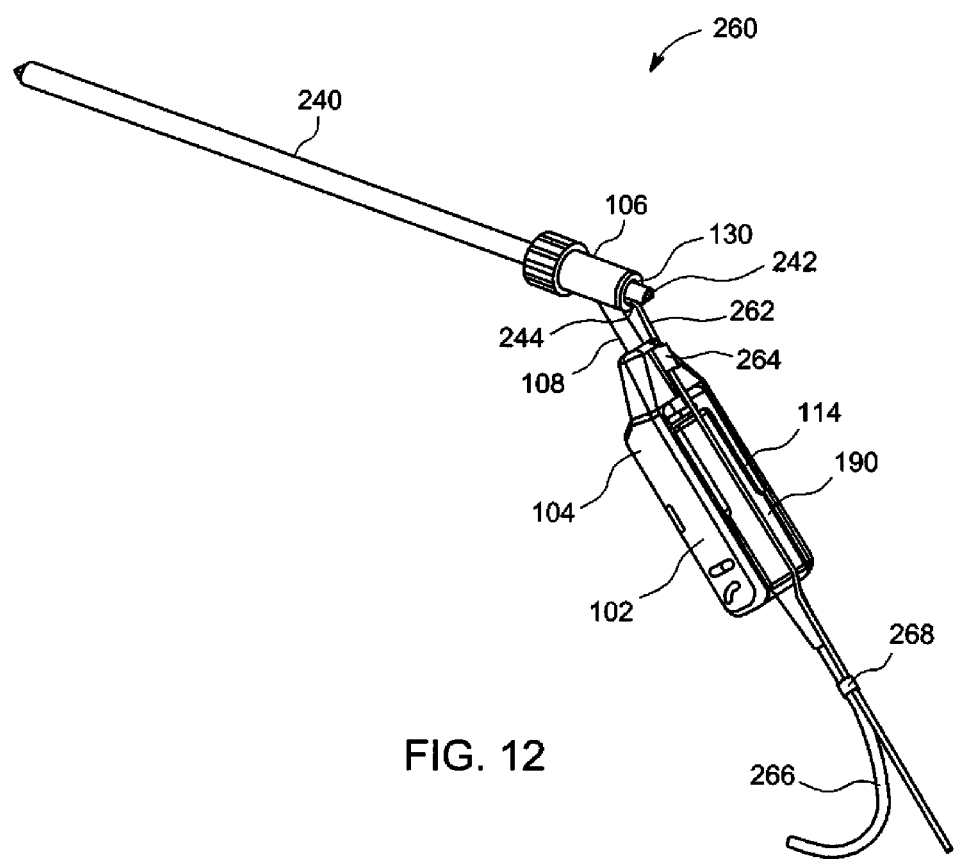
FIG. 12 is a perspective view of an exemplary embodiment of a trackable instrument guide system with a guide instrument and an electromagnetic sensor assembly attached to an instrument guide apparatus.

FIG. 12 illustrates an exemplary embodiment of a trackable instrument guide system 260 with a guide instrument 240 and an electromagnetic sensor assembly 190 attached to the instrument guide apparatus 102. The instrument guide system 260 comprises a handle assembly 104, an instrument attachment assembly 106, a shaft 108 connecting the handle assembly 104 to the instrument attachment assembly 106, an electromagnetic sensor assembly 190 removably mounted within a docking station 114 of the handle assembly 104, and a guide instrument 240 removably attachable within the central bore 130 of the instrument attachment assembly 106. The instrument guide system 260 is configured to receive a first surgical instrument (not shown) within the first bore 242 of the guide instrument 240 and a second surgical instrument 262 within the second bore 244 of the guide instrument 240. The instrument guide system 260 is intended for multiple uses in surgical procedures to guide instrumentation with surgical navigation. The second bore 244 may accept a second surgical instrument 262, such as a catheter, endoscope, fiber optic light cable, fiberscope or video endoscope, extending therethrough.

In an embodiment, the second bore 244 may accept a high intensity fiber optic light cable through which a high intensity light is beamed to brilliantly illuminate the patient's anatomy in the surgical field of interest. The high intensity fiber optic light cable may be integrated with a light port and endoscopic telescope to visualize the patient's anatomy in the surgical field of interest for display on the surgical navigation system's display. This endoscopic view may be mixed with 2D fluoro images, 3D fluoro images, CT images, MR images, PET images, ultrasound images, or fused together in the case of advanced percutaneous MIS procedures.

The second surgical instrument 262, such as a catheter, endoscope, fiber optic light cable, fiberscope, or video endoscope, extends from the second bore 244 and distal end 248 of the guide instrument 240 across the handle assembly 104. The handle assembly 104 may include at least one clip 264 to hold the second surgical instrument 262 against the handle assembly 104. The catheter, endoscope, fiber optic light cable, fiberscope, or video endoscope 262 may also be attached to a cable 266 from the electromagnetic sensor assembly 190 with a fastener 268. The catheter, endoscope, fiber optic light cable, fiberscope, or video endoscope may be coupled to a video and/or light source unit (not shown).

These instrument guides 210, 240 and trackable instrument guide systems 230, 260 may be used in various surgical procedures including abdominal, cervical, thoracic, lumbar, and extremity procedures.

For simple and complex surgical applications the navigated instrument guide system provides new technology of real-time virtual instrument visualization on a computer screen. The benefits of navigation are less x-ray radiation explosion to the surgeon and the patient, less time for fluoroscopic manipulations, up to four simultaneous multi-planar x-ray guidance views versus single view, enhanced precision of instrument placement, stronger purchase for screw placement, ability to save trajectories in all views, capability to project forward a virtual trajectory from the guide tip and ability to estimate instrument depth.

It should be appreciated that according to alternate embodiments, the at least one electromagnetic sensor may be an electromagnetic receiver, an electromagnetic generator (transmitter), or any combination thereof. Likewise, it should be appreciated that according to alternate embodiments, the at least one electromagnetic field generator may be an electromagnetic receiver, an electromagnetic transmitter or any combination of an electromagnetic field generator (transmitter) and an electromagnetic receiver.

Several embodiments are described above with reference to drawings. These drawings illustrate certain details of specific embodiments that implement the systems, methods and programs of the invention. However, the drawings should not be construed as imposing on the invention any limitations associated with features shown in the drawings. This disclosure contemplates methods, systems and program products on any machine-readable media for accomplishing its operations. As noted above, the embodiments of the may be implemented using an existing computer processor, or by a special purpose computer processor incorporated for this or another purpose or by a hardwired system.

Embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated.

Those skilled in the art will appreciate that the embodiments disclosed herein may be applied to the formation of any surgical navigation system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

What is claimed is:

1. An instrument guide apparatus comprising:
a handle assembly;
an instrument attachment assembly, wherein the instrument attachment assembly includes a cylindrical member having a central bore extending therethrough for removably attaching an instrument therein;
a shaft having a first end connected to the handle assembly and a second end, opposite the first end, connected to the instrument attachment assembly; and
a docking station formed within the handle assembly, wherein the docking station includes an opening for removably engaging an electromagnetic sensor assembly therein, and wherein a flexible switch member extends from the handle assembly over a portion of the docking station so as to function as a push button switch when the electromagnetic sensor assembly is disposed in the docking station, wherein the docking station includes a locking member at one end of the opening for locking the electromagnetic sensor assembly in place and an engagement member at the opposite end thereof for keeping the electromagnetic sensor assembly engaged within the opening.

2. The instrument guide apparatus of claim 1, wherein the handle assembly includes a handle body and a handle stem.

3. The instrument guide apparatus of claim 2, wherein the handle body includes the docking station.

4. The instrument guide apparatus of claim 2, wherein the flexible switch member functions as the push button switch to activate a feature in a surgical navigation software program.

5. The instrument guide apparatus of claim 1, wherein the shaft extends up through an opening in the instrument attachment assembly and includes a tab for securing the instrument within the central bore of the cylindrical member.

6. The instrument guide apparatus of claim 1, wherein the instrument attachment assembly further includes a fastening member extending around an outer surface of the cylindrical member for removably fastening the instrument to the instrument attachment assembly.

7. A surgical navigation system, comprising:
an imaging apparatus; and
a navigation apparatus connected to an instrument guide apparatus, the instrument guide apparatus comprising:
a handle assembly;
an instrument attachment assembly, wherein the instrument attachment assembly includes a cylindrical member having a central bore extending therethrough for removably attaching an instrument therein;
a shaft having a first end connected to the handle assembly and a second end, opposite the first end, connected to the instrument attachment assembly; and
a docking station formed within the handle assembly, wherein the docking station includes an opening for removably engaging an electromagnetic sensor assembly therein, and wherein a flexible switch member extends from the handle assembly over a portion of the docking station so as to function as a push button switch when the electromagnetic sensor assembly is disposed in the docking station, wherein the docking station includes a locking member at one end of the opening for locking the electromagnetic sensor assembly in place and an engagement member at the opposite end thereof for keeping the electromagnetic sensor assembly engaged within the opening.

8. The surgical navigation system of claim 7, wherein the handle assembly includes a handle body and a handle stem.

9. The surgical navigation system of claim 8, wherein the handle body includes the docking station.

10. The surgical navigation system of claim 7, wherein the flexible switch member functions as the push button switch to activate a feature in a surgical navigation software program.

11. The surgical navigation system of claim 7, wherein the shaft extends up through an opening in the instrument attachment assembly and includes a tab for securing the instrument within the central bore of the cylindrical member.

12. The surgical navigation system of claim 7, wherein the instrument attachment assembly further includes a fastening member extending around an outer surface of the cylindrical member for removably fastening the instrument to the instrument attachment assembly.

* * * * *

UNITED STATES PATENT AND TRADEMARK OFFICE
CERTIFICATE OF CORRECTION

PATENT NO. : 8,821,511 B2
APPLICATION NO. : 11/686468
DATED : September 2, 2014
INVENTOR(S) : von Jako et al.

Page 1 of 1

It is certified that error appears in the above-identified patent and that said Letters Patent is hereby corrected as shown below:

In the specification

Column 11, line 65, delete "262".

Signed and Sealed this
Twenty-fourth Day of March, 2015

Michelle K. Lee
*Director of the United States Patent and Trademark Office*